United States Patent
Shaaban et al.

(10) Patent No.: US 12,006,293 B1
(45) Date of Patent: Jun. 11, 2024

(54) BIS DISELENIDE-BASED SCHIFF BASES AS DEUBIQUITINATION SIGNALING PATHWAY MODULATORS

(71) Applicant: KING FAISAL UNIVERSITY, Al-Ahsa (SA)

(72) Inventors: Saad Shaaban, Al-Ahsa (SA); Amr Negm, Al-Ahsa (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 18/545,056

(22) Filed: Dec. 19, 2023

(51) Int. Cl.
  C07D 231/12 (2006.01)
  A61K 31/4155 (2006.01)
  A61K 31/4375 (2006.01)
  C07D 213/65 (2006.01)
  C07D 401/14 (2006.01)

(52) U.S. Cl.
  CPC ........ *C07D 231/12* (2013.01); *A61K 31/4155* (2013.01); *A61K 31/4375* (2013.01); *C07D 213/65* (2013.01); *C07D 401/14* (2013.01)

(58) Field of Classification Search
  CPC ................ C07D 231/12; C07D 213/65; C07D 4001/14; A61K 31/4155; A61K 31/4375
  See application file for complete search history.

(56) References Cited

U.S. PATENT DOCUMENTS 11,814,346 B1 * 11/2023 Shabaan ................ C09K 19/40
2019/0091688 A1    3/2019 Bandara et al.

OTHER PUBLICATIONS

Pablo Garnica et al.; "Organoseleno cytostatic derivatives: Autophagic cell death with AMPK and JNK activation"; European Journal of Medicinal Chemistry, vol. 175, Aug. 1, 2019, pp. 234-246.

Marta Díaz et al.; "Thermal stability and decomposition of urea, thiourea and selenourea analogous diselenide derivatives"; Journal of Thermal Analysis and Calorimetry vol. 127, pp. 1663-1674 (2017).

Maximilian Roca Jungfer et al. ;"Reactions of Schiff Base-Substituted Diselenides and -tellurides with Ni(II), Pd(II) and Pt(II) Phosphine Complexes"; vol. 2020, Issue 45, Dec. 7, 2020, pp. 4303-4312.

João M. Anghinoni et al. ; "Recent Advances in the Synthesis and Antioxidant Activity of Low Molecular Mass Organoselenium Molecules"; Molecules 2023, 28(21), 7349; https://doi.org/10.3390/molecules28217349 Revised: Oct. 17, 2023 / Accepted: Oct. 26, 2023 / Published: Oct. 30, 2023.

Eduardo H.G. da Cruz et al.; "Synthesis and antitumor activity of selenium-containing quinone-based triazoles possessing two redox centres, and their mechanistic insights"; Jun. 2016 European Journal of Medicinal Chemistry 122 DOI:10.1016/j.ejmech.2016.06.019.

Mónica Álvarez-Pérez et al.; "Selenides and Diselenides: A Review of Their Anticancer and Chemopreventive Activity"; Molecules. Mar. 2018; 23(3): 628. Published online Mar. 10, 2018. doi: 10.3390/molecules23030628.

Guoxiong Hua et al.; "Novel Five- and Six-Membered Rings of Phosphorus-Selenium Heterocycles from Selenation of Amido-Schiff Bases"; ACS Omega 2020, 5, 20, 11737-11744 Publication Date: May 12, 2020.

* cited by examiner

*Primary Examiner* — D Margaret M Seaman
(74) *Attorney, Agent, or Firm* — Nath, Goldberg & Meyer; Richard C. Litman

(57) ABSTRACT

Diselenide organo compounds, their synthesis, and their use as deubiquitination signaling pathway modulators and anticancer agents.

20 Claims, No Drawings

BIS DISELENIDE-BASED SCHIFF BASES AS DEUBIQUITINATION SIGNALING PATHWAY MODULATORS

BACKGROUND

1. Field

The present disclosure relates to bis diselenide-based schiff bases, their synthesis, and their use as deubiquitination signaling pathway modulators and as anti-cancer agents.

2. Description of the Related Art

There remains an ongoing need for new therapeutically active agents for treating a variety of diseases, disorders, and conditions including, but not limited to, various forms of cancer, various microbial infections, and the like.

Deubiquitinating enzymes (DUBs) are a large group of proteases that cleave ubiquitin from proteins. They are also known as deubiquitinating peptidases, deubiquitinating isopeptidases, deubiquitinases, ubiquitin proteases, ubiquitin hydrolases, or ubiquitin isopeptidases. DUBs are crucial regulators of both the ubiquitination-mediated degradation and other functions. They are responsible for deubiquitination and have emerged as crucial players in tumor growth, progression, and immune evasion.

Deubiquitination enzymes (DUBs) have emerged as promising targets for cancer therapy. Inhibition of DUBs has demonstrated their potential to selectively target cancer cells. Notably, USP7 (Ubiquitin-Specific Protease 7) and USP9X (Ubiquitin-Specific Protease 9X) are DUBs that play critical roles in regulating the stability and activity of various proteins implicated in cancer related signaling pathways, including important tumor suppressors like p53, NF-KB, and the Wnt/β-catenin pathway. Recent studies revealed that diselenides exhibited preferential cellular growth inhibition towards cancer cells with higher selectivity. The chemistry of heterocycles lies at the heart of drug discovery. Investigation of fortunate organic compounds for drug discovery has been a rapidly emerging theme in medicinal chemistry.

Schiff bases are a kind of organic dye generally characterized by their nitrogen-carbon double bond (—N═C—). Schiff bases especially those linked with heterocyclic moiety exhibited various pharmacological and biological activities such as antibacterial, cytotoxic effects, antitumor, antifungal, antimalarial, anticonvulsant, antioxidant, and anti-inflammatory.

Thus, new molecules having desired therapeutic activities and solving the aforementioned problems are desired.

SUMMARY

Presented herein are novel Bis diselenide-based Schiff bases designed to inhibit USP7 (Ubiquitin-Specific Protease 7) and USP9X (Ubiquitin-Specific Protease 9X), ultimately restoring p53 function and inducing cancer cell death. These compounds possess the capacity to modulate signaling pathways crucial to cancer progression, such as the Wnt/β-catenin and p53 pathways that restore normal cellular functions.

The product described herein is a new Schiff base derivative produced in order to provide a limited library of "drug-like" substances. Bis(4-aminophenyl)diselenide was used as the building blocks for the synthesis of Schiff bases described herein. Bis diselenide-based Schiff bases were synthesized from the condensation of bis(4-aminophenyl) diselenide with 4-chloro-1H-pyrazole-3-carboxaldehyde, 3-hydroxypyridine-2-carboxaldehyde, and 2-pyridin-3-yl-1H-indole-3-carboxaldehyde. In certain embodiments, the bis diselenide-based Schiff bases were synthesized from the condensation of bis(4-aminophenyl)diselenide (2 equivalents) with one equivalent of 4-chloro-1H-pyrazole-3-carboxaldehyde, 3-hydroxypyridine-2-carboxaldehyde, and 2-pyridin-3-yl-1H-indole-3-carboxaldehyde, respectively.

In an embodiment, the present subject matter relates to a diselenide organo compound having the formula:

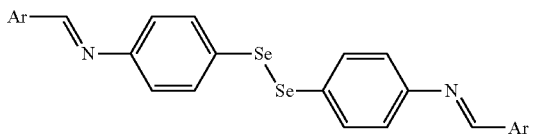

wherein Ar is selected from the group consisting of a pyrazole, a pyridine, and an indole, and wherein said Ar is optionally substituted with a chlorine, a hydoxy, or a pyridine.

In another embodiment of the present subject matter the diselenide organo compound may be selected from the group consisting of:

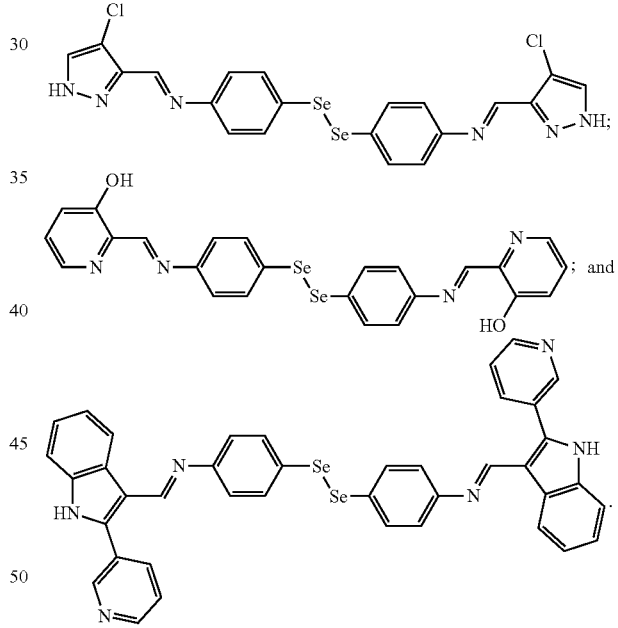

In another embodiment, the present subject matter relates to a pharmaceutically acceptable composition comprising a therapeutically effective amount of a diselenide organo compound as described herein and a pharmaceutically acceptable carrier.

In an additional embodiment, the present subject matter relates to a method of inhibiting Ubiquitin-specific proteases in a subject comprising administering to a subject in need thereof a therapeutically effective amount of a diselenide organo compound as described herein. The Ubiquitin-specific proteases may be selected from the group consisting of USP7 and USP9X.

In a further embodiment, the present subject matter relates to a method of restoring p53 function in a subject, the method comprising administering to a subject in need thereof a therapeutically effective amount of a diselenide organo compound as described herein.

In still another embodiment, the present subject matter relates to a method of inducing cancer death in a subject, the method including administering to a subject in need thereof a therapeutically effective amount of a diselenide organo compound as described herein.

In another embodiment, the present subject matter related to a method of treating cancer in a subject, the method comprising administering to a subject in need thereof a therapeutically effective amount of a diselenide organo compound as described herein.

In one more embodiment, the present subject matter relates to a method of making the diselenide organo compounds as described herein, the method comprising: adding an aldehyde to a bis diselenide Schiff base in ethanol to obtain a reaction mixture; adding a catalyst to the reaction mixture; refluxing the reaction mixture; cooling the reaction mixture to obtain a formed precipitate; filtering and recrystallizing the formed precipitate from ethanol; and obtaining the diselenide organo compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inhibiting certain enzyme activity and/or treating cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Presented herein are novel Bis diselenide-based Schiff bases designed to inhibit USP7 and USP9X, ultimately restoring p53 function and inducing cancer cell death. These compounds possess the capacity to modulate signaling pathways crucial to cancer progression, such as the Wnt/ß-catenin and p53 pathways that restore normal cellular functions.

The product described herein is a new Schiff base derivative produced in order to provide a limited library of "drug-like" substances. Bis(4-aminophenyl)diselenide was used as the building blocks for the synthesis of Schiff bases described herein. Bis diselenide-based Schiff bases were synthesized from the condensation of bis(4-aminophenyl)diselenide with 4-chloro-1H-pyrazole-3-carboxaldehyde, 3-hydroxypyridine-2-carboxaldehyde, and 2-pyridin-3-yl-1H-indole-3-carboxaldehyde. In certain embodiments, the bis diselenide-based Schiff bases were synthesized from the condensation of bis(4-aminophenyl)diselenide (2 equivalents) with one equivalent of 4-chloro-1H-pyrazole-3-carboxaldehyde, 3-hydroxypyridine-2-carboxaldehyde, and 2-pyridin-3-yl-1H-indole-3-carboxaldehyde, respectively.

In an embodiment, the present subject matter relates to a diselenide organo compound having the formula I:

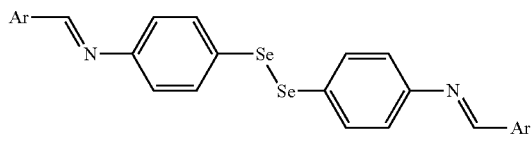

wherein Ar is selected from the group consisting of a pyrazole, a pyridine, and an indole, and wherein said Ar is optionally substituted with a chlorine, a hydroxy, or a pyridine.

In another embodiment, the present subject matter relates to a diselenide organo compound selected from the group consisting of:

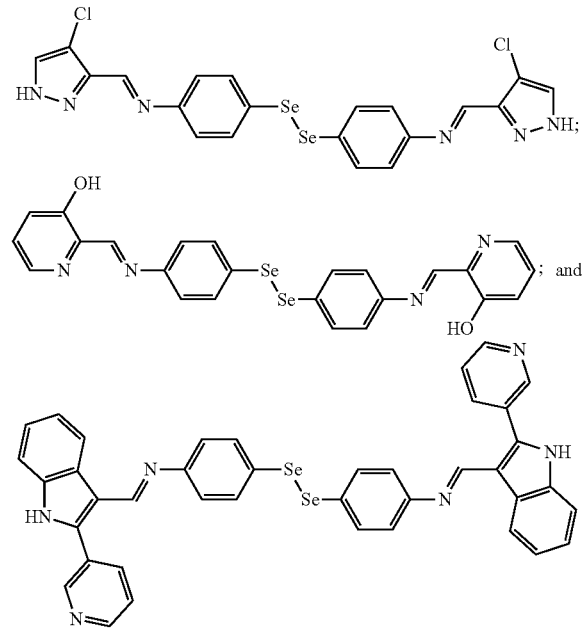

In yet another embodiment, the present subject matter relates to a pharmaceutically acceptable composition comprising a therapeutically effective amount of a diselenide organo compound described herein and a pharmaceutically acceptable carrier. The diselenide organo compound of the pharmaceutically acceptable composition can be selected from the group consisting of:

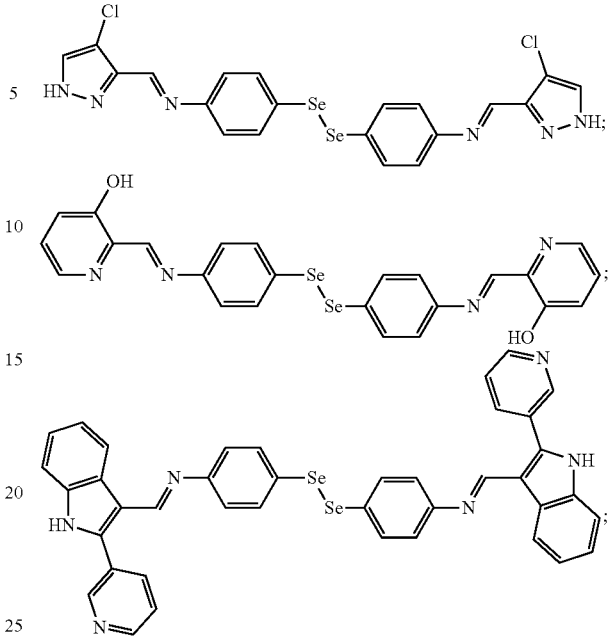

a combination thereof.

In still another embodiment, the present subject matter relates to a method of inhibiting Ubiquitin-specific proteases in a subject comprising administering to a subject in need thereof a therapeutically effective amount of a diselenide organo compound as described herein. The Ubiquitin-specific proteases may be selected from the group consisting of USP7 and USP9X.

The method of inhibiting Ubiquitin-specific proteases can include administering a diselenide organo compound selected from the group consisting of:

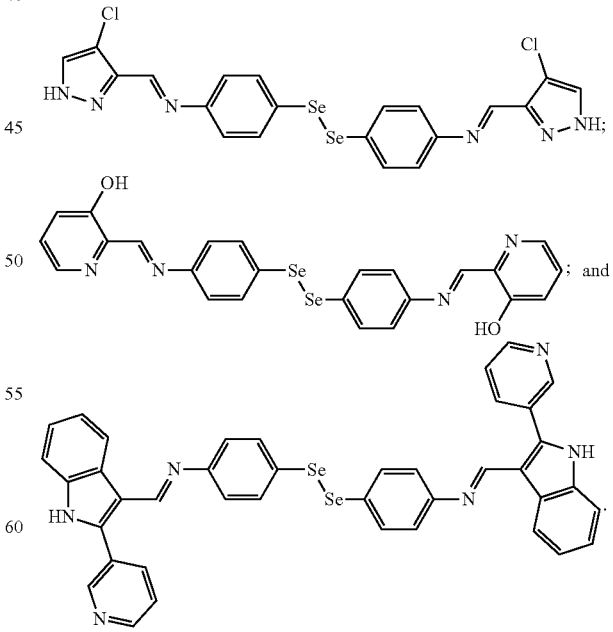

In a further embodiment, the present subject matter relates to a method of restoring p53 function in a subject, the method comprising administering to a subject in need thereof a therapeutically effective amount of a diselenide organo compound as described herein.

The method of restoring p53 function can include administering a diselenide organo compound selected from the group consisting of:

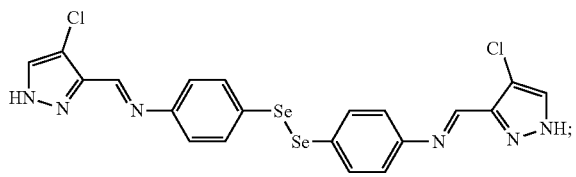

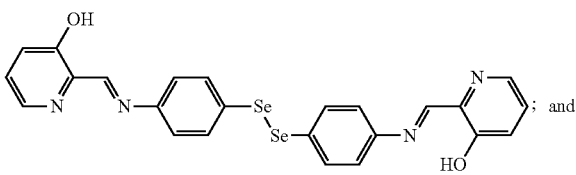

; and

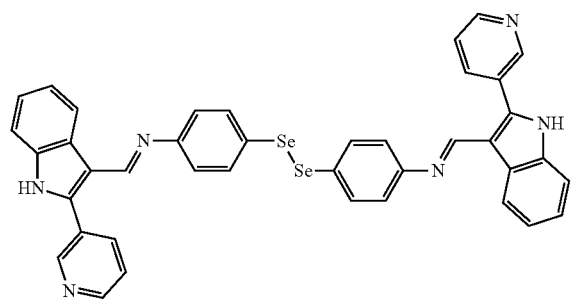

In another embodiment, the present subject matter relates to a method of inducing cancer death in a subject, the method comprises administering to a subject in need thereof a therapeutically effective amount of a diselenide organo compound as described herein.

The method of inducing cancer death in a subject can include administering a diselenide organo compound selected from the group consisting of:

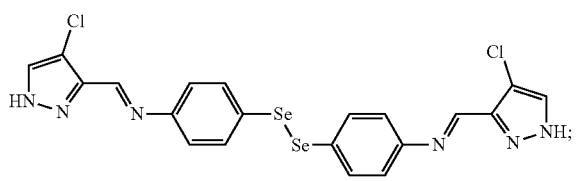

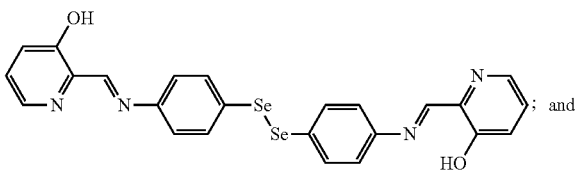

; and

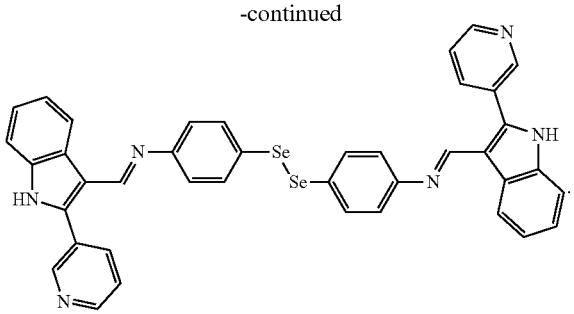

In yet another embodiment, the present subject matter relates to a method of treating cancer in a subject, the method comprises administering to a subject in need thereof a therapeutically effective amount of a diselenide organo compound as described herein.

The method of treating cancer in a subject can include administering a diselenide organo compound selected from the group consisting of:

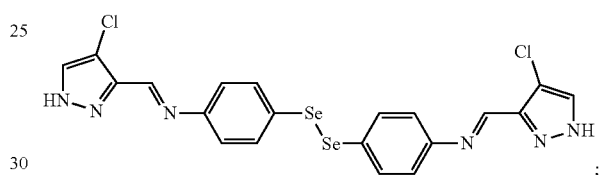

;

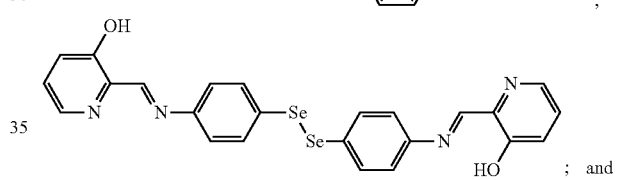

; and

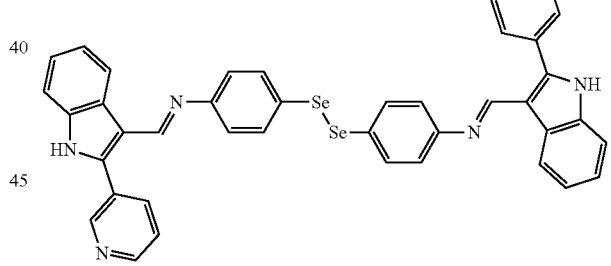

.

In this regard, the present subject matter is further directed to pharmaceutical compositions comprising a therapeutically effective amount of a compound as described herein together with one or more pharmaceutically acceptable carriers, excipients, or vehicles. In some embodiments, the present compositions can be used for combination therapy, where other therapeutic and/or prophylactic ingredients can be included therein. IN other embodiments, the present compositions can include more than one of the present compounds.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to inhibit enzyme activity and/or treat cancer. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for inhibiting an enzyme activity and/or treating cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In one embodiment, bis(4-aminophenyl)diselenide 1 can be used as starting blocks for the synthesis of the Schiff bases 2a-c as illustrated in Scheme 1. Bis diselenide-based Schiff bases 2a, 2b, and 2c are synthesized from the condensation of bis(4-aminophenyl)diselenide 1 with one equivalent of 4-chloro-1H-pyrazole-3-carboxaldehyde, 3-hydroxypyridine-2-carboxaldehyde, and 2-pyridin-3-yl-1H-indole-3-carboxaldehyde, respectively according to the Scheme 1 below.

Scheme 1

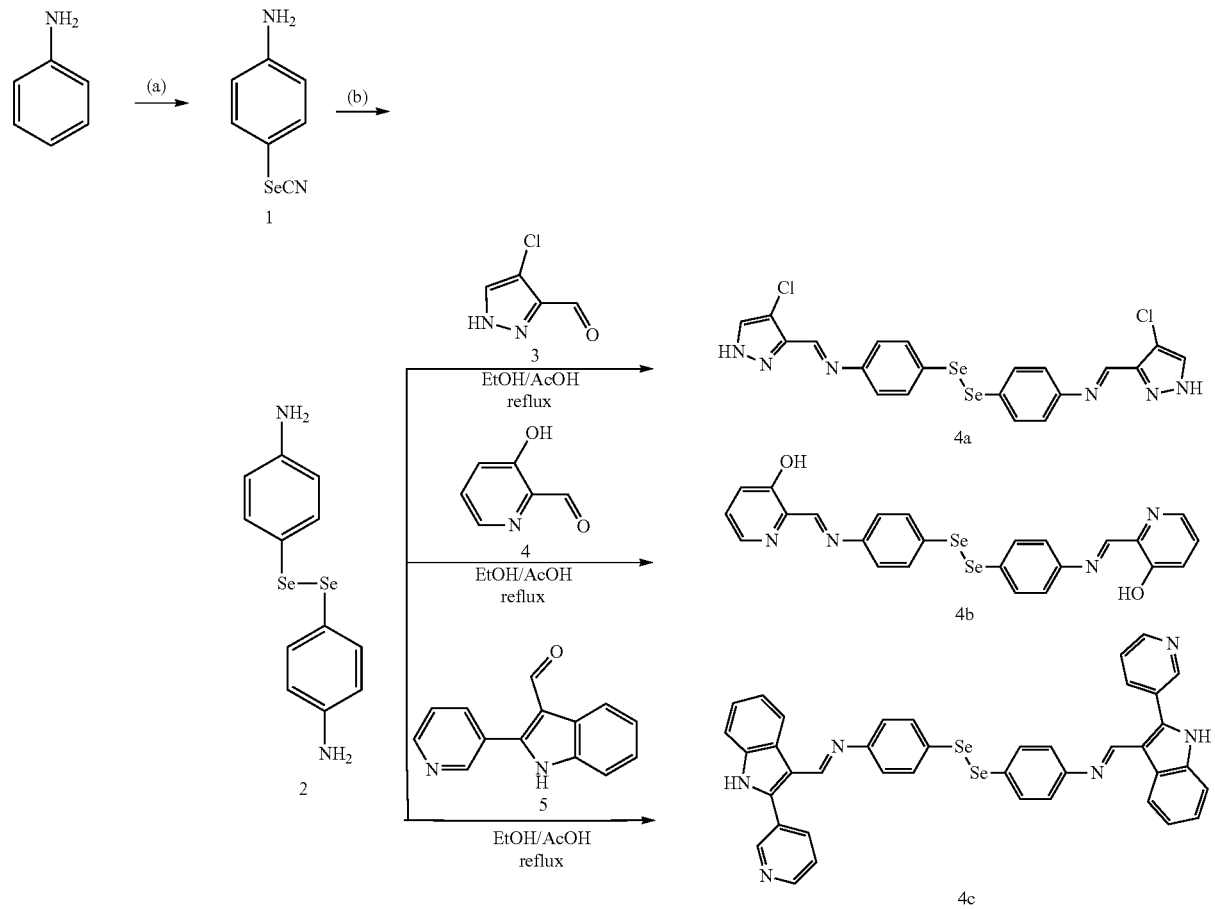

Specifically, synthesis commences with causing an aniline reaction with triselenium diselenide, prepared in situ from malononitrile, selenium dioxide, and DMSO. After 15 minutes the reaction is filtered, and the filtrate is diluted with ice-cold water to give the corresponding selenocyanate 1.

The formed precipitate (selenocyanate) is dissolved in methanol and NaOH is added. Then the mixture is stirred for at least about 4 hours. The resulting yellow precipitate is dried under vacuum to give diselenide 1.

Next, the condensation of one equivalent of the commercially available aldehydes 4-chloro-1H-pyrazole-3-carbaldehyde (3), 3-hydroxypicolinaldehyde (4), and 2-(pyridin-3-yl)-1H-indole-3-carbaldehyde (5) with diselenide 1 affords the corresponding bis Schiff bases 4a-c. The reaction proceeds in ethanol using a catalytic amount of acetic acid. The reaction is refluxed for at least about 6 hours and after cooling, the formed precipitate as filtered and recrystallized from ethanol to give Schiff bases 4a-c.

In one more embodiment, the present subject matter relates to a method of making the diselenide organo compounds, the method comprising: adding an aldehyde to a bis diselenide Schiff base in ethanol to obtain a reaction mixture; adding a catalyst to the reaction mixture; refluxing the reaction mixture; cooling the reaction mixture to obtain a formed precipitate; filtering and recrystallizing the formed precipitate from ethanol; and obtaining the diselenide organo compound.

The present production methods can be further seen by referring to the following Scheme 2:

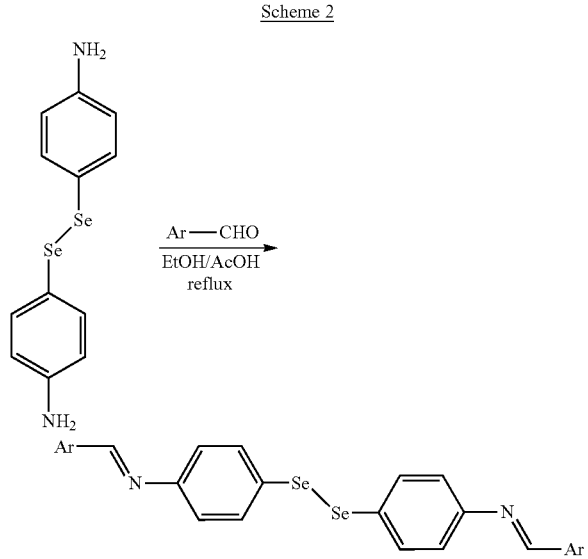

In an embodiment of the present production methods, the aldehyde may be 4-chloro-1H-pyrazole-3-carboxaldehyde and the diselenide organo compound may be diselenide bis (4-chloro-1H-pyrazole-3-carboxaldehyde).

In another embodiment, the aldehyde may be 3-hydroxypyridine-2-carboxaldehyde and the diselenide organo compound may be diselenide bis (3-hydroxypyridine-2-carboxaldehyde).

In still another embodiment, the aldehyde may be 2-pyridin-3-yl-1H-indole-3-carboxaldehyde and the diselenide organo compound may be diselenide bis (2-pyridin-3-yl-1H-indole-3-carboxaldehyde).

In further embodiments, about 1 equivalent of the aldehyde may be added to about 0.5 equivalents of the diselenide Schiff base.

The following examples relate to various methods of manufacturing the specific compounds and application of the same, as described herein. All compound numbers expressed herein are with reference to the synthetic pathway figures shown above.

EXAMPLES

Example 1

Preparation of the Diselenide 2

Diselenide 2 was synthesized according to the modified reported literature methods as follow: reaction of aniline (72 mmol) with triselenium diselenide, prepared in situ from malononitrile (19.6 mmol), selenium dioxide (20 mmol), DMSO (10 mL). After 15 minutes the reaction was filtered, and the filtrate was diluted with 250 mL ice-cold water to give the corresponding selenocyanate 1. The formed precipitate (selenocyanate) was dissolved in methanol 200 mL and NaOH (80 mmol) was added. The mixture was allowed to be stirred for 4 hours. The resulting yellow precipitate was dried under vacuum to give diselenide 1.

Example 2

Condensation of Aldehydes

The condensation of one equivalent of the commercially available aldehydes 4-chloro-1H-pyrazole-3-carbaldehyde (3), 3-hydroxypicolinaldehyde (4), and 2-(pyridin-3-yl)-1H-indole-3-carbaldehyde (5) with 0.5 equivalent of diselenide 1 afforded the corresponding bis Schiff bases 4a-c. The reaction proceeded in ethanol using a catalytic amount of acetic acid. The reaction was refluxed for 6 hours and after cooling, the formed precipitate was filtered and recrystallized from ethanol to give 4a-c.

It is to be understood that the bis diselenide-based Schiff base compounds, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A diselenide organo compound having the formula:

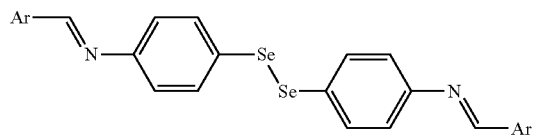

wherein Ar is selected from the group consisting of a pyrazole, a pyridine, and an indole, and wherein said Ar is optionally substituted with a chlorine, a hydroxy, or a pyridine.

2. The diselenide organo compound of claim 1, wherein the diselenide organo compound is selected from the group consisting of:

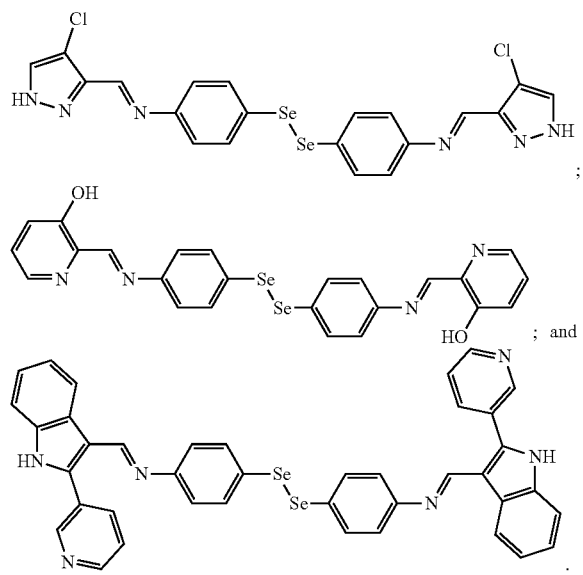

3. A pharmaceutically acceptable composition comprising a therapeutically effective amount of the diselenide organo compound of claim 1 and a pharmaceutically acceptable carrier.

4. The pharmaceutically acceptable composition of claim 3, wherein the diselenide organo compound is selected from the group consisting of:

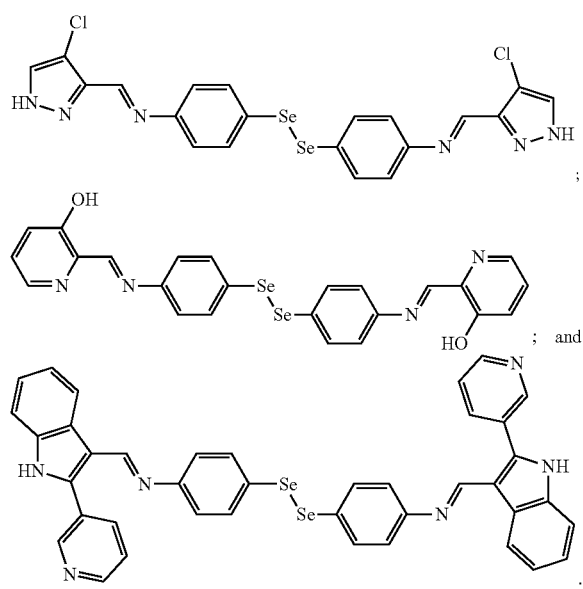

5. A method of inhibiting Ubiquitin-specific proteases in a subject comprising administering to a subject in need thereof a therapeutically effective amount of the diselenide organo compound of claim 1.

6. The method of inhibiting Ubiquitin-specific proteases in a patient of claim 5, wherein the Ubiquitin-specific proteases are selected from the group consisting of USP7 and USP9X.

7. The method of inhibiting Ubiquitin-specific proteases of claim 5, wherein the diselenide organo compound is selected from the group consisting of:

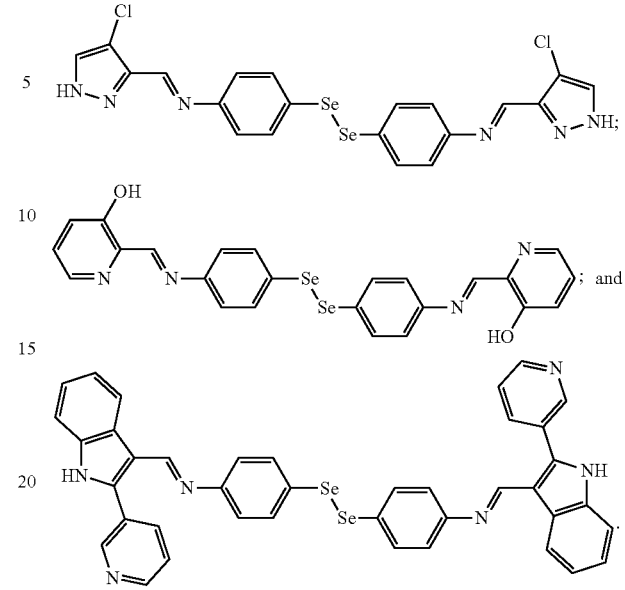

8. A method of restoring p53 function in a subject, the method comprising administering to a subject in need thereof a therapeutically effective amount of the diselenide organo compound of claim 1.

9. The method of restoring p53 function of claim 8, wherein the diselenide organo compound is selected from the group consisting of:

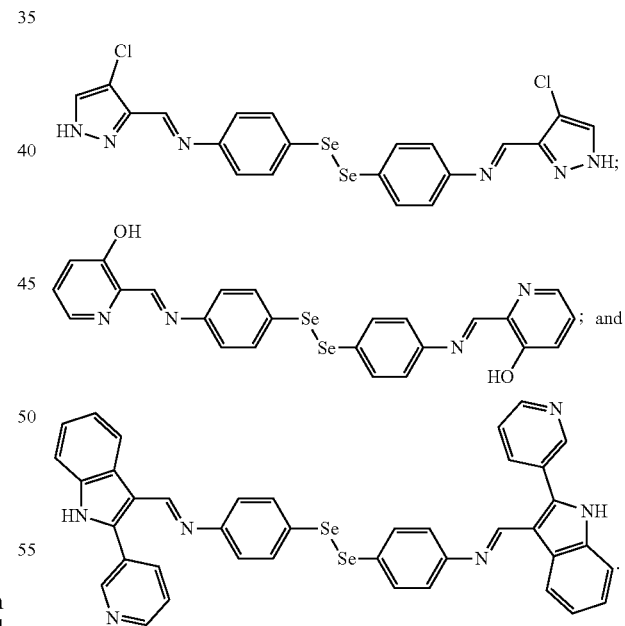

10. A method of inducing cancer death in a subject, the method comprising administering to a subject in need thereof a therapeutically effective amount of the diselenide organo compound of claim 1.

11. The method of inducting cancer death of claim 10, wherein the diselenide organo compound is selected from the group consisting of:

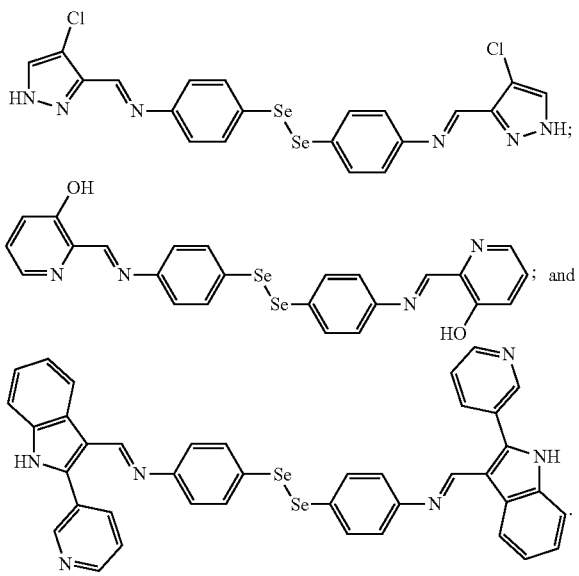

12. A method of treating cancer in a subject, the method comprising administering to a subject in need thereof a therapeutically effective amount of the diselenide organo compound of claim 1.

13. The method of treating cancer of claim 12, wherein the diselenide organo compound is selected from the group consisting of:

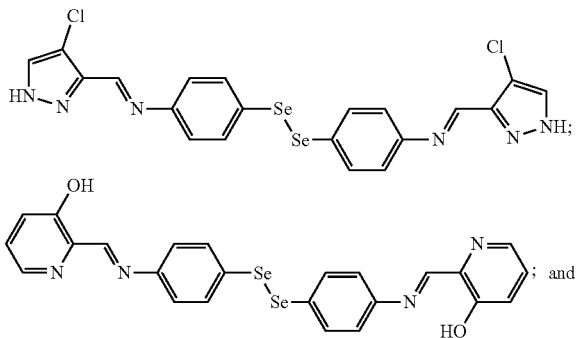

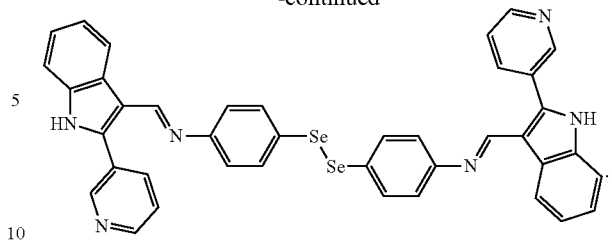

14. A method of making the diselenide organo compound of claim 1, the method comprising:
adding an aldehyde to a bis diselenide Schiff base in ethanol to obtain a reaction mixture;
adding a catalyst to the reaction mixture;
refluxing the reaction mixture;
cooling the reaction mixture to obtain a formed precipitate;
filtering and recrystallizing the formed precipitate from ethanol; and
obtaining the diselenide organo compound.

15. The method of making the diselenide organo compounds of claim 14, wherein the aldehyde is 4-chloro-1H-pyrazole-3-carboxaldehyde and the diselenide organo compound is diselenide bis (4-chloro-1H-pyrazole-3-carboxaldehyde).

16. The method of making the diselenide organo compounds of claim 14, wherein the aldehyde is 3-hydroxypyridine-2-carboxaldehyde and the diselenide organo compound is diselenide bis (3-hydroxypyridine-2-carboxaldehyde).

17. The method of making the diselenide organo compounds of claim 14, wherein the aldehyde is 2-pyridin-3-yl-1H-indole-3-carboxaldehyde and the diselenide organo compound is diselenide bis (2-pyridin-3-yl-1H-indole-3-carboxaldehyde).

18. The method of making the diselenide organo compounds of claim 14, wherein the catalyst is acetic acid.

19. The method of making the diselenide organo compounds of claim 14, wherein about 1 equivalent of the aldehyde is added to about –0.5 equivalents of the diselenide Schiff base.

20. The method of making the diselenide organo compounds of claim 14, wherein the reaction mixture is refluxed for at least 6 hours.

\* \* \* \* \*